(12) United States Patent
Mueller

(10) Patent No.: US 7,071,706 B2
(45) Date of Patent: Jul. 4, 2006

(54) MEASURING DEVICE FOR RAPID NON-DESTRUCTIVE MEASUREMENT OF THE CONTENTS OF CAPSULES

(75) Inventor: Hanns Walter Mueller, Mainz (DE)

(73) Assignee: Boehringer Ingelheim International, GmbH, Ingelheim (DE)

( * ) Notice: Subject to any disclaimer, the term of this patent is extended or adjusted under 35 U.S.C. 154(b) by 220 days.

(21) Appl. No.: 10/852,508

(22) Filed: May 24, 2004

(65) Prior Publication Data

US 2005/0154555 A1    Jul. 14, 2005

Related U.S. Application Data

(60) Provisional application No. 60/499,070, filed on Aug. 29, 2003.

(30) Foreign Application Priority Data

Jun. 3, 2003    (EP) .................................. 03012566

(51) Int. Cl.
*G01R 27/04*    (2006.01)
*G01G 7/02*    (2006.01)
(52) U.S. Cl. ..................... 324/637; 324/644; 73/865; 702/23
(58) Field of Classification Search ............... 324/637, 324/640, 644, 641; 73/865; 702/23
See application file for complete search history.

(56) References Cited

U.S. PATENT DOCUMENTS

| | | | |
|---|---|---|---|
| 5,397,993 A | 3/1995 | Tews et al. | |
| 5,515,740 A | 5/1996 | Gamberini | |
| 5,554,935 A * | 9/1996 | Kraszewski et al. | 324/637 |
| 5,602,485 A * | 2/1997 | Mayer et al. | 324/663 |
| 5,852,259 A * | 12/1998 | Yanase | 177/145 |
| 6,114,636 A | 9/2000 | Cane' et al. | |
| 6,691,563 B1 * | 2/2004 | Trabelsi et al. | 73/73 |
| 2001/0000946 A1 | 5/2001 | Moeller et al. | |
| 2004/0225454 A1* | 11/2004 | Herrmann et al. | 702/23 |

FOREIGN PATENT DOCUMENTS

DE    40 04 119 A1    8/1991
WO    WO 97/31244 A1    8/1997

OTHER PUBLICATIONS

Enlish Abstract for DE 40 04 119 A1.

* cited by examiner

*Primary Examiner*—Anjan Deb
(74) *Attorney, Agent, or Firm*—Michael P. Morris; Mary-Ellen M. Devlin; Philip I. Datlow

(57) ABSTRACT

The invention relates to a process for the non-destructive net weighing of capsules using microwaves.

8 Claims, 3 Drawing Sheets

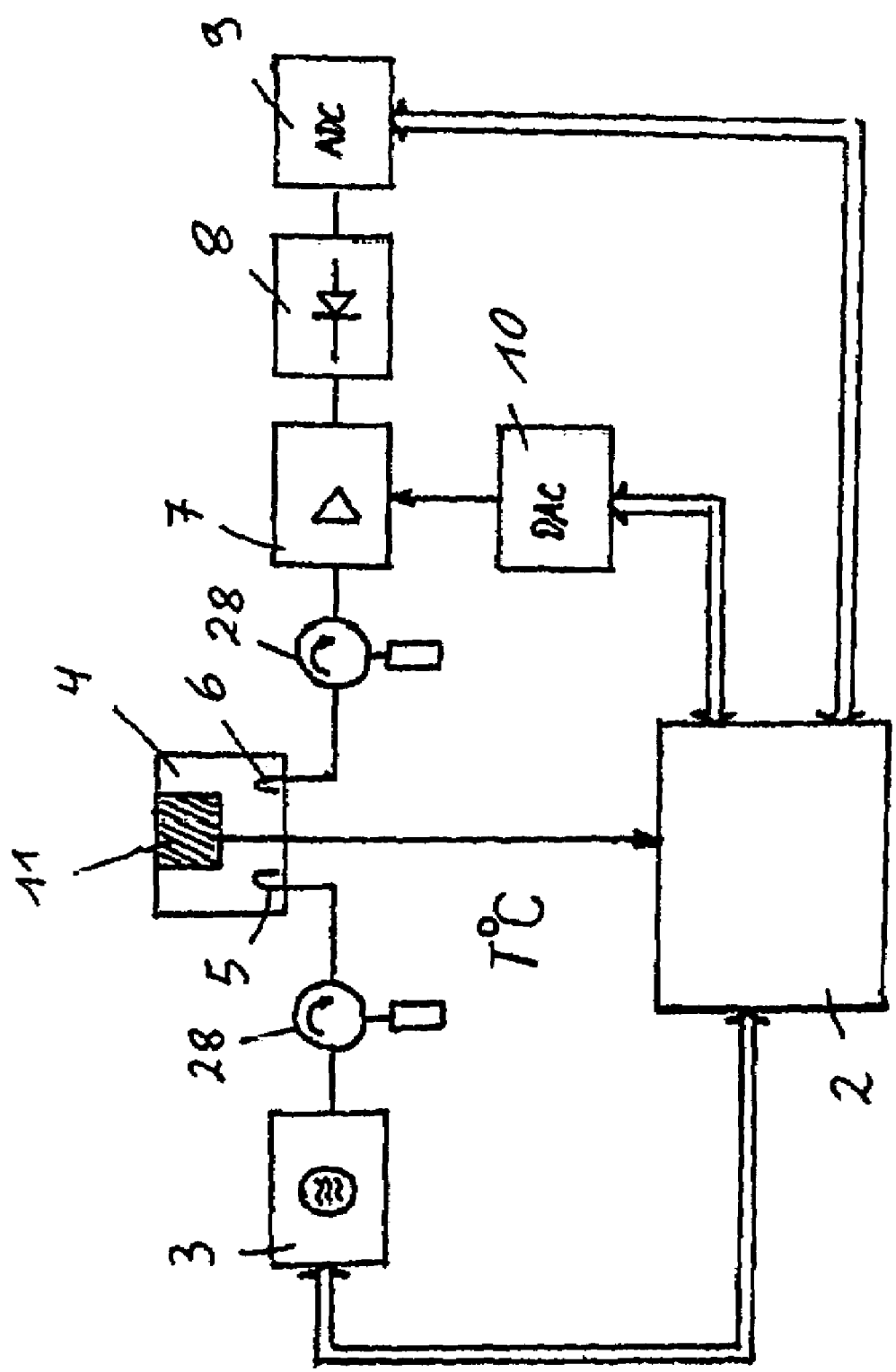
Fig 1: Plan of the layout for the microwave process

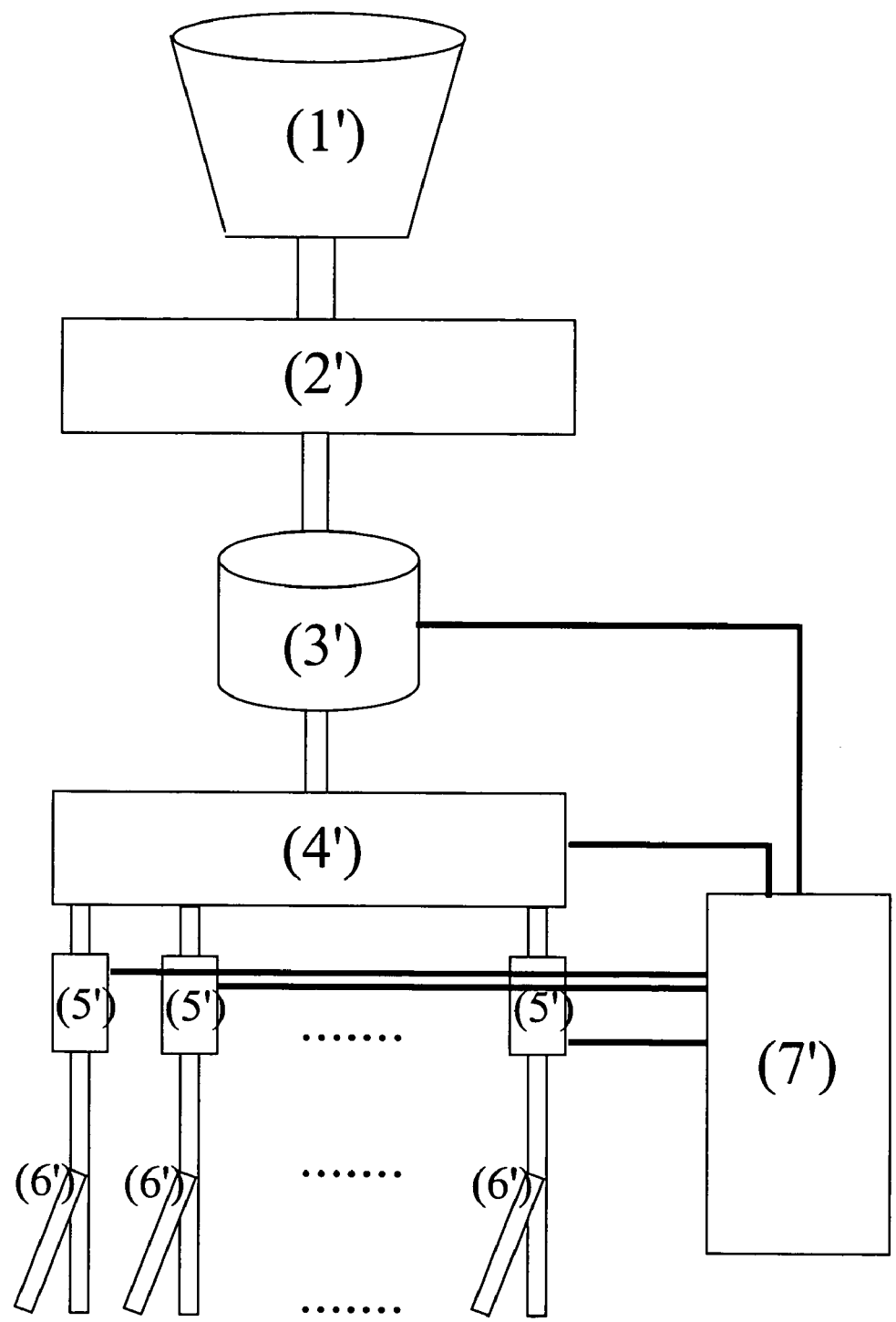
Fig 2: Plan of the connection of the microwave detector and weighing cells

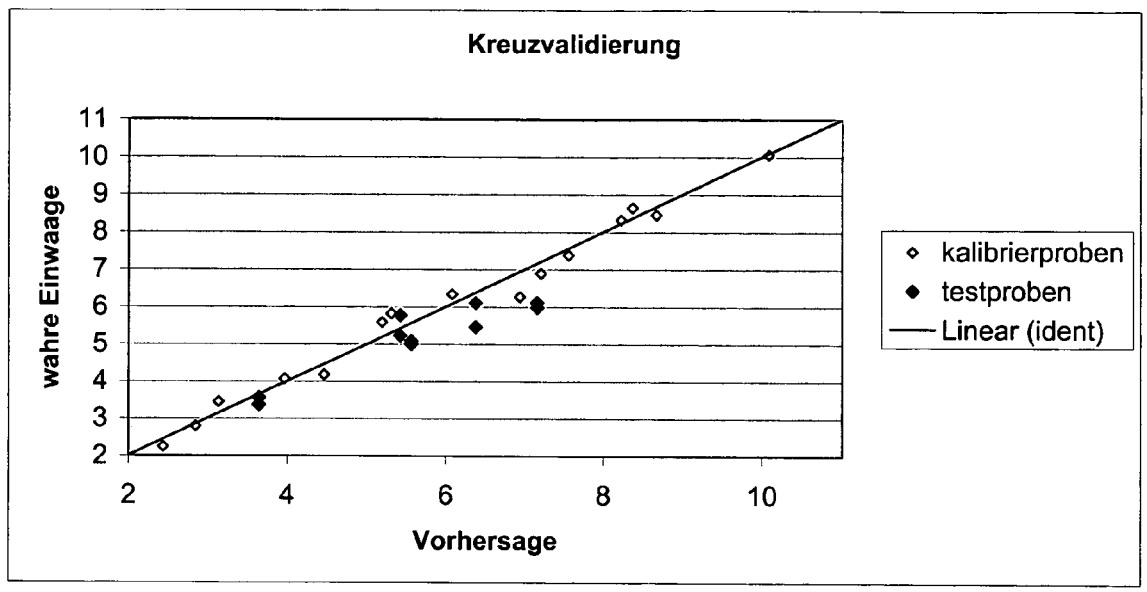
Fig.3: Cross-calibration with 15 calibrating samples and validation with 10 test samples
Kreuzvalidierung = cross-validation
wahre Einwaage = true weight
Vorhersage = prediction
Kalibrierproben = calibrating samples
Testproben = test samples
Linear (ident) = linear (ident)

MEASURING DEVICE FOR RAPID NON-DESTRUCTIVE MEASUREMENT OF THE CONTENTS OF CAPSULES

RELATED APPLICATIONS

Benefit of U.S. Provisional Application Ser. No. 60/499,070, filed on Aug. 29, 2003 is hereby claimed, and which application is incorporated herein in its entirety.

FIELD OF THE INVENTION

The invention relates to a process for the non-destructive net weighing of capsules using microwaves.

BACKGROUND TO THE INVENTION

In many industrial manufacturing processes it is particularly important to know the net weight of packed goods (e.g. bulk goods, foodstuffs, etc.). When the tare weight is negligibly small compared with the net weight, gross weighing of the packed goods is generally sufficient. However, if the wrappings or packaging are very small, as in the case of pharmaceutical formulations containing active substances, such as capsules, for example, the ratio between the surface area and the volume is shifted considerably towards the surface area, and the tare weight is easily a multiple of the net weight. In such cases, fluctuations in the tare weight cannot be disregarded. The net weight must therefore be determined either by directly weighing the net contents or by weighing the object to be measured before and after packaging (determining the tare and gross weights).

Naturally, net weighing will always be carried out on the filling or packing machine where the actual metering process takes place. The same is also true, however, of gross/tare weighing when operating at high production rates, as otherwise the proper association between the tare and gross measurements of the individual items could only be achieved with difficulty or at considerable expense.

When high production rates (e.g. 100,000 items/hour or more) are required while at the same time small quantities in the mg range are being weighed out, the measuring apparatus is subject to extreme demands in terms of precision and speed. For example, online gross/tare weighing systems on capsule filling machines in which a capacitive measuring system is used are known in the prior art. The substance to be measured is passed through a capacitor before and after filling and the mass introduced is calculated from its change in capacity. However, it has been found that processes of this kind are only suitable for use with amounts of more than 50 mg. Modern gravimetric weighing cells meet significantly higher accuracy requirements. However, they operate at a low speed of only a few capsules per second. Significantly higher throughput speeds could be achieved by providing weighing cells of this kind in parallel, but gravimetric weighing cells have the limitation of being highly sensitive to vibrations and having to be operated in cycles rather than continuously. Consequently, gravimetric weighing cells can only be used to a very limited extent on continuously operating capsule filling machines.

There is thus a need for a weighing method which—when detached from the filling machine and operating as a stand-alone solution—is capable of determining the contents of filled and sealed capsules.

BRIEF DESCRIPTION OF THE DRAWINGS

FIG. 1 shows the diagrammatic structure of such an apparatus

As shown in FIG. 1, this apparatus is characterized by a variable-frequency microwave generator (3) which can be digitally tuned by a processor (2), this generator being connected to a coupling probe (5) which is disposed in an applicator (4) for measuring the measuring signals F and B of a sample (11), said applicator (4) having another coupling probe (6) which is connected via a microwave amplifier or attenuator (7) to a detector diode (8) the signal output of which is connected to the processor (2). As shown in FIG. 1, the detector diode (8) may be connected to the processor (2) via an analogue-to-digital converter (9). The attenuator (7) may be connected to the processor (2) via a digital-to-analogue converter (10), as shown in FIG. 1. A circulator (28) for uncoupling is disposed between the microwave generator (3) and the coupling probe (5) and between the coupling probe (6) and the microwave amplifier or attenuator (7). To determine the gross weight signal C, gravimetric weighing cells may be used which determine the weight with a standard deviation of ±0.1 mg.

FIG. 2 shows the diagrammatic plan of the coupling of the microwave process to the gross weighing. Using a separating unit (2') the filled and sealed capsules are guided serially and/or individually from a hopper (1') through the microwave resonator (3'). An adjacent distributor unit (4') as used in current capsule weighing machines arranges the capsules for parallel transportation and distributes them onto several pathways where the gravimetric weighing cells (5') are located. A computer-aided data collecting unit (7') which is connected to the units (3'), (4') and (5') ensures that the measurements are correctly assigned to the individual capsules and performs the evaluation. Capsules of the wrong net weight are diverted into a reject channel (6'). The term microwave resonator (3') denotes an apparatus according to FIG. 1.

FIG. 3 depicts cross-calibration with 15 calibrating samples and validation with 10 test samples.

DESCRIPTION OF THE INVENTION

The problem stated above is solved by the process according to the invention. The invention relates to a process for the non-destructive net weighing of capsules using microwaves, wherein in a first step of the process variable frequency electromagnetic radiation is generated in a microwave generator under the control of a processor and is supplied to a probe applicator in the form of a resonator, the microwave signal leaving the applicator being supplied to a detector diode from whose signals b(0) and f(0) are determined by the computer as primary measurement values by means of an analogue-to-digital converter, b(0) being the half-power width at the resonance frequency f(0) of the applicator which is operatively connected to a measuring probe, characterized in that a sample of material is connected to the resonator such that the electric field of the resonator runs generally parallel to the surface on passing into the material of the probe and in that, from the primary measurement values b(0) and f(0), the measuring signals $$F = f(L) - f(0) \text{ or } B = b(0) - b(L)$$

are obtained, where F and B denote the microwave measuring signals of the detuning and propagation of the resonance, with f(L) and b(L) equal to constant material-dependent reference values, and wherein in a second step gravimetric gross weighing is carried out in order to determine the gross weight signal $$C = m_T + m_N,$$

wherein the magnitude $m_T$ represents the mass of the empty packaging and the magnitude $m_N$ represents the net mass to be determined, and finally from the measuring signals F, B and C the net mass $m_N$ to be determined is computed according to the following equation $$m_N = \alpha F + \beta B + \gamma C + \delta,$$

the coefficients $\alpha$, $\beta$, $\gamma$ and $\delta$ having been determined beforehand by calibration of the measuring system by linear regression from a series of measurements with reference samples of known net weight.

The measuring signals F and B may be determined using apparatus as disclosed for example in DE 4004119.

This process is suitable for contents in the mg range. It operates at high speed and can be used even when the weight of the packaging or the empty capsule far exceeds the weight of the capsule contents.

The particular value of the process is that the necessary measurement can be carried out at high speed and with precision so that even amounts in the mg range can be processed. Fluctuations in the moisture content of the product or packaging are also compensated by the process according to the invention.

The data sets obtained by the process according to the invention are evaluated as described hereinafter.

The masses of the packaging (tare) and goods for measurement (net weight) are designated $m_T$ and $m_N$. Either the packaging or the contents must contain water. The mass of water contained either in the empty capsule or in the filling is hereinafter designated $m_{H2O}$.

The two measuring signals determined by the microwave measuring method for detuning and propagating the resonance are hereinafter referred to as $F = f(L) - f(0)$ or $B = b(0) - b(L)$ and the result of the gross weighing is designated C.

The detuning of the microwave resonator F and also the propagation of the resonance B are proportional to the mass of the sample introduced into the resonator. Thus the two microwave measuring signals can be represented in the following form:

$$F = f_T m_T + f_{H2O} m_{H2O} + f_N m_N, \quad (1)$$

$$B = b_T m_T + b_{H2O} m_{H2O} + b_N m_N, \quad (2)$$

The coefficients $f_T$, $f_{H2O}$, $f_N$ and $b_T$, $b_{H2O}$, $b_N$ denote the respective substance-specific proportionality constants.

As the microwave attenuation depends primarily on the water content of the product being measured, the measuring signal B is essentially determined by the term $b_{H2O} m_{H2O}$ in equation (2). Fluctuations in the moisture content of either the product or the packaging are thus compensated by taking account of the measured value B.

For the gross weight signal $$C = m_T + m_N. \quad (3)$$

After inversion of the linear equation system (1), (2) and (3) and resolution according to the net weight sought, $m_N$ is obtained as a linear combination of the measuring data F, B and C obtained, in the form $$m_N = \alpha F + \beta B + \gamma C + \delta \quad (4)$$

For calibration the $\alpha$, $\beta$, $\gamma$ and $\delta$ in equation (4) are determined by linear regression from a measuring series with reference samples of known net weight. The coefficient $\delta$ takes account of any possible shift in the calibration caused by other influencing factors (e.g. temperature).

As the microwave detuning F is always proportional to the respective dielectric constant (DC) of the materials introduced into the resonator, the operating principle of the proposed apparatus is guaranteed when the DCs of the packing and contents are sufficiently different.

By capsules are meant, within the scope of the present invention, sealed capsules characterized in that they contain a quantity of a powder. The material from which these capsules are made is selected according to the invention from among gelatin, cellulose derivatives, starch, starch derivatives, chitosan and synthetic plastics. If gelatin is used as the capsule material, it may be used in admixture with other additives selected from among polyethyleneglycol (PEG), preferably PEG 3350, glycerol, sorbitol, propyleneglycol, PEO-PPO block copolymers and other polyalcohols and polyethers. Within the scope of the present invention gelatin is used particularly preferably in admixture with PEG, preferably PEG 3350. A gelatin capsule according to the invention preferably contains PEG in an amount of 1–10% (wt.-%), preferably 3–8%. Particularly preferred gelatin capsules contain PEG in an amount of 4–6%, a PEG content of about 5% being most preferred according to the invention. If cellulose derivatives are used as the capsule material, it is preferable to use hydroxypropylmethylcellulose, hydroxypropylcellulose, methylcellulose, hydroxymethylcellulose and hydroxyethylcellulose. In this case, hydroxypropylmethylcellulose (HPMC), particularly preferably HPMC 2910 is used as the capsule material. If synthetic plastics are used as the capsule material, these are preferably selected according to the invention from among polyethylene, polycarbonate, polyester, polypropylene and polyethylene terephthalate. Particularly preferred synthetic plastics for the capsules for inhalation according to the invention are polyethylene, polycarbonate or polyethylene terephthalate. If polyethylene is used as one of the particularly preferred capsule materials according to the invention, polyethylene with a density of between 900 and 1000 kg/m3, preferably from 940–980 kg/m3, particularly preferably 960 kg/m3 is preferably used (high-density polyethylene).

The empty capsules may be prepared by methods known in the art. For example, possible production methods include the dipping method, blow molding, injection molding, extrusion and deep drawing, all of which are known in the art.

The process according to the invention for net weighing capsules is aimed at determining the precise weight or mass $m_N$ of the powder contained in the capsules. This powder is preferably a powder intended for inhalation which contains a pharmaceutically acceptable excipient in addition to an active substance.

Examples of pharmaceutically acceptable excipients include, for example, monosaccharides (e.g. glucose or arabinose), disaccharides (e.g. lactose, saccharose, maltose, trehalose), oligo- and polysaccharides (e.g. dextrane), polyalcohols (e.g. sorbitol, mannitol, xylitol), salts (e.g. sodium chloride, calcium carbonate), or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

The active substances within the scope of the present invention are compounds which are preferably selected from among the anticholinergics, betamimetics, dopamine agonists, antiallergics, leukotriene antagonists and corticosteroids and optionally combinations of active substances thereof.

Examples of preferred anticholinergics are compounds selected from among the tiotropium salts, ipratropium salts, oxitropium salts, salts of the compounds known from WO 02/32899 tropenol N-methyl-2,2-diphenylpropionate, scopine N-methyl-2,2-diphenylpropionate, scopine N-methyl-2-fluoro-2,2-diphenylacetate and tropenol N-methyl-2-fluoro-2,2-diphenylacetate as well as salts of the compounds known from WO 02/32899 tropenol N-methyl-3,3',4,4'-tetrafluorobenzilate, scopine N-methyl-3,3',4,4'-tetrafluorobenzilate; scopine N-methyl-4,4'-dichlorobenzilate, scopine N-methyl-4,4'-difluorobenzilate, tropenol N-methyl-3,3'-difluorobenzilate, scopine N-methyl-3,3'-difluorobenzilate and tropenol N-ethyl-4,4'-difluorobenzilate, optionally in the form of their hydrates and solvates.

By salts are meant those compounds which contain, in addition to the abovementioned cations, as counter-ion, an anion with a single negative charge selected from among the chloride, bromide and methanesulphonate.

Particularly preferably the active substances within the scope of the present invention are the bromides or methanesulphonates of the abovementioned structures.

Of exceptional interest within the scope of the present invention are, for example, the anticholinergics tiotropium bromide, ipratropium bromide, oxitropium bromide, 2,2-diphenylpropionate tropenol-methobromide, scopine 2,2-diphenylpropionate-methobromide, scopine 2-fluoro-2,2-diphenylacetate-methobromide, tropenol 2-fluoro-2,2-diphenylacetate-methobromide, tropenol 3,3',4,4'-tetrafluorobenzilate-methobromide, scopine 3,3',4,4'-tetrafluorobenzilate-methobromide; scopine 4,4'-dichlorobenzilate-methobromide, scopine 4,4'-difluorobenzilate-methobromide, tropenol 3,3'-difluorobenzilate-methobromide, scopine 3,3'-difluorobenzilate-methobromide and tropenol 4,4'-difluorobenzilate-ethylbromide, while tiotropium bromide, ipratropium bromide, tropenol 2,2-diphenylpropionate-methobromide, scopine 2,2-diphenylpropionate-methobromide, scopine 2-fluoro-2,2-diphenylacetate-methobromide and tropenol 2-fluoro-2,2-diphenylacetate-methobromide are particularly important. Of outstanding importance here is tiotropium bromide, most particularly in the form of its crystalline monohydrate known from WO 02/30928.

Examples of betamimetics which may be used according to the invention are preferably compounds selected from among bambuterol, bitolterol, carbuterol, clenbuterol, fenoterol, formoterol, hexoprenaline, ibuterol, pirbuterol, procaterol, reproterol, salbutamol, salmeterol, sulphonterol, terbutaline, tulobuterol, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind selected from among fenoterol, formoterol, salmeterol, salbutamol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

For example, the acid addition salts of the betamimetics are selected from among the hydrochloride, hydrobromide, sulphate, phosphate, fumarate, methanesulphonate and xinafoate are preferred according to the invention. In the case of formoterol, the salts selected from among the hydrochloride, sulphate and fumarate are particularly preferred, especially the hydrochloride and fumarate. Of outstanding importance according to the invention is formoterol fumarate. In the case of salmeterol, the salts selected from among the hydrochloride, sulphate and xinafoate are particularly preferred, especially the xinafoate.

Within the scope of the present invention, the corticosteroids which may be used according to the invention are compounds selected from among flunisolide, beclomethasone, triamcinolone, budesonide, fluticasone, mometasone, ciclesonide, rofleponide, GW 215864, KSR 592, ST-126 and dexamethasone. The preferred corticosteroids within the scope of the present invention are those selected from among flunisolide, beclomethasone, triamcinolone, budesonide, fluticasone, mometasone, ciclesonide and dexamethasone, while budesonide, fluticasone, mometasone and ciclesonide, especially budesonide and fluticasone, are of particular importance. The term steroids may be used on its own, within the scope of the present patent application, instead of the term corticosteroids. Any reference to steroids within the scope of the present invention also includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. The corticosteroids may optionally also be in the form of their hydrates.

Within the scope of the present invention, the term dopamine agonists denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of antiallergic agents which may be used according to the invention include epinastin, cetirizin, azelastin, fexofenadin, levocabastin, loratadine, mizolastin, ketotifen, emedastin, dimetinden, clemastine, bamipin, cexchlorpheniramine, pheniramine, doxylamine, chlorophenoxamine, dimenhydrinate, diphenhydramine, promethazine, ebastin, desloratidine and meclizine. Preferred antiallergic agents which may be used within the scope of the present invention are selected from among epinastin, cetirizin, azelastin, fexofenadin, levocabastin, loratadine, ebastin, desloratidine and mizolastin, epinastin and desloratidine being particularly preferred. Any reference to the abovementioned antiallergic agents also includes, within the scope of the present invention, a reference to any pharmacologically acceptable acid addition salts thereof which may exist.

The embodiments that follow serve to illustrate the invention more fully. The following measurements were obtained on a set of 25 capsules filled with an inhalable powder containing tiotropium bromide. The microwave measurements F and B were measured using a microwave moisture measuring apparatus MW 3010, the microwave electronic evaluator MW 3010 and the resonator E83/8, made and supplied by Messrs TEWS Elektronik (Sperberhorst 10, D-22459 Hamburg). The gross weighings to determine the value C were carried out using an AX105 analytical balance made by Messrs Mettler Toledo GmbH (Im Langacher, CH-8606 Greifensee, Switzerland) with a reduced read-off accuracy of 0.1 mg.

In order to calibrate the apparatus and evaluate the accuracy which could be achieved with the process it was necessary to know the true net weights $m_N$ of the 25 capsules. For this purpose the capsules were filled manually using a hand-operated powder pipette. The net weight of the filling was determined by weighing the individual capsules before and after filling on the above-mentioned Mettler analytical balance with a read-off accuracy of 0.01 mg.

Table 1 combines all the measurements and weights obtained. The first 15 samples were used to calibrate the instruments. For this purpose the coefficients $\alpha$, $\beta$, $\gamma$ and $\delta$ from equation (4) were calculated by linear regression from the measured values F, B, C with the known net weight values $m_N$.

From this the following was obtained as the coming together of the measuring signal and the weight:

$$m_N = -0.18105 \frac{mg}{MHz} * A + 0.0438 \frac{mg}{MHz} * B + 1.470 * C. \qquad (5)$$

$\sigma_{calibration\ data}$=0.33 mg was obtained as the standard deviation between the 15 calibration data and the predictions calculated after calibration (cross calibration).

After the calibration carried out in this way the remaining 10 capsules were used to test the accuracy of the proposed weighing method. The comparison between the true weighed values and the predictions based on the calibration (5) yields a standard deviation of $\sigma_{test\ samples}$=0.68 mg. FIG. 3 brings all the calibration and test data together in the cross-validation diagram.

TABLE 1

Measured values of the 25 calibration and test samples

| | Sample | Net [mg] analytical balance | Gross [mg] analytical balance | Tare [mg] analytical balance | Microwave F [MHz] | Microwave B [MHz] | Gross [mg] C [mg] | Prediction $m_N$ [mg] according to equation (5) |
|---|---|---|---|---|---|---|---|---|
| Calibration samples | 1 | 2.44 | 50.23 | 47.79 | 418.8594 | 103.9680936 | 50 | 2.24 |
| | 2 | 2.85 | 51.06 | 48.21 | 424.9063 | 104.6123785 | 51.1 | 2.79 |
| | 3 | 3.14 | 50.31 | 47.17 | 413.8125 | 100.6091802 | 50.3 | 3.45 |
| | 4 | 3.97 | 52.04 | 48.07 | 425.9063 | 104.3166723 | 52.1 | 4.07 |
| | 5 | 4.46 | 52.29 | 47.83 | 424.8594 | 102.5303456 | 52.1 | 4.18 |
| | 6 | 5.19 | 52.46 | 47.27 | 416.9063 | 98.36373737 | 52.2 | 5.58 |
| | 7 | 5.31 | 53.51 | 48.2 | 429.9063 | 103.8392956 | 53.8 | 5.82 |
| | 8 | 6.08 | 54.36 | 48.28 | 430.875 | 102.979476 | 54.3 | 6.34 |
| | 9 | 6.94 | 53.2 | 46.26 | 421.9375 | 101.2003059 | 53.2 | 6.27 |
| | 10 | 7.56 | 54.7 | 47.14 | 427.9375 | 101.101946 | 54.7 | 7.38 |
| | 11 | 8.23 | 56.18 | 47.95 | 434.9531 | 101.3368326 | 56.2 | 8.33 |
| | 12 | 7.21 | 55.41 | 48.2 | 435.9453 | 102.809727 | 55.3 | 6.89 |
| | 13 | 8.37 | 56.63 | 48.26 | 434.9375 | 101.9294894 | 56.4 | 8.65 |
| | 14 | 8.67 | 56.97 | 48.3 | 440 | 101.7243854 | 56.9 | 8.46 |
| | 15 | 10.08 | 58.3 | 48.22 | 440.9297 | 101.7071026 | 58.1 | 10.06 |
| Test samples | 16 | 7.16 | 56.27 | 49.11 | 451.0703 | 111.1018252 | 56.3 | 5.98 |
| | 17 | 7.16 | 56.27 | 49.11 | 451.1563 | 111.1708615 | 56.4 | 6.12 |
| | 18 | 5.56 | 53.51 | 47.95 | 432.0078 | 107.2317522 | 53.4 | 5.00 |
| | 19 | 5.56 | 53.51 | 47.95 | 434.0625 | 107.6035326 | 53.7 | 5.09 |
| | 20 | 6.38 | 54.16 | 47.78 | 433.0313 | 106.4290683 | 54.3 | 6.10 |
| | 21 | 6.38 | 54.16 | 47.78 | 435.0625 | 106.8360262 | 54.1 | 5.46 |
| | 22 | 5.42 | 52.74 | 47.32 | 424.0703 | 103.103133 | 52.7 | 5.23 |
| | 23 | 5.42 | 52.74 | 47.32 | 426.125 | 103.9186604 | 53.3 | 5.77 |

TABLE 1-continued

Measured values of the 25 calibration and test samples

| Sample | Net [mg] analytical balance | Gross [mg] analytical balance | Tare [mg] analytical balance | Microwave F [MHz] | Microwave B [MHz] | Gross [mg] C [mg] | Prediction $m_N$ [mg] according to equation (5) |
|---|---|---|---|---|---|---|---|
| 24 | 3.65 | 51.65 | 48 | 426.0156 | 105.6539372 | 51.6 | 3.37 |
| 25 | 3.65 | 51.65 | 48 | 424.0938 | 105.4024385 | 51.5 | 3.56 |

The invention claimed is:

1. a process for the non-destructive net weighing of capsules, comprising:
   (a) generating a variable frequency electromagnetic radiation in a microwave generator under the control of a processor and supplying said radiation to a probe applicator in the form of a resonator, the microwave signal leaving the applicator being supplied to a detector diode from whose signals b(0) and f(0) are determined by the computer as primary measurement values by means of an analogue-to-digital converter wherein b(0) is the half-power width at the resonant frequency f(0) of the applicator;
   (b) determining the measuring signals according to the equation:

$F = f(L) - f(0)$ or $B = b(0) - b(L)$ wherein F and B are the microwave measuring signals of the detuning and propagation of the resonance, with f(L) and b(L) being equal to constant material-dependent reference values;
   (c) determining the gross weight signal by weighing the gravimetric gross and applying it in the following equation:

$C = mT + m_N$, wherein the magnitude $m_T$ represents the mass of the empty packaging and the magnitude $m_N$ represents the net mass to be determined; and
   (d) determining the net mass $m_N$ according to the following equation $m_N = \alpha F + \beta B + \gamma C + \delta$ wherein the measuring signals F, B, and C are determined above and the coefficients $\alpha$, $\beta$, $\gamma$ and $\delta$ having been determined by calibration of the measuring system by linear regression from a measuring series with reference samples of known net weight.

2. A process according to claim 1, characterized in that filled capsules are weighed, the material from which the capsules are made is selected from the group consisting of gelatine, cellulose derivatives, starch, starch derivatives, chitosan and synthetic plastics.

3. A process according to claim 2 characterized in that the capsules hold a powder which contains an active substance and optionally a pharmaceutically acceptable excipient.

4. A process according to claim 3, characterized in that the active substance is selected from the group comprising the anticholinergics, betamimetics, dopamine agonists, anti-allergics, leukotriene antagonists and corticosteroids and optionally combinations of active substances thereof.

5. Process according to claim 1 characterized in that the measured signal values F and B are determined by means of an apparatus which is characterised by a variable-frequency microwave generator (3) which can be digitally tuned by a processor (2), this generator being connected to a coupling probe (5) which is disposed in an applicator (4) for measuring the measuring signals F and B of a sample (11), said applicator (4) having another coupling probe (6) which is connected via a microwave amplifier or attenuator (7) to a detector diode (8) the signal output of which is connected to the processor (2).

6. Process according to claim 1 characterized in that to determine the gross weight signal C a gravimetric weighing cell is used which determines the weight with a standard deviation of ±0.1 mg.

7. Process according to claim 1 characterized in that it is carried out using an apparatus which comprises a hopper (1') from which the filled and sealed capsules are guided serially and/or individually by means of a separating unit (2') through the microwave resonator (3'), which also comprises an adjacent distributor unit (4') by means of which the capsules are arranged parallel for transporting and by means of which the capsules are distributed onto several pathways where the gravimetric weighing cells (5') are located, and which also comprises a computer-aided data collecting unit (7') which is connected to connected to the units (3'), (4') and (5') and ensures that the measurements are correctly assigned to the individual capsules and performs the evaluation and which finally has a reject channel (6') through which capsules of the wrong weight are rejected.

8. Apparatus for carrying out the process according to claim 1, which comprises a hopper (1') from which the filled and sealed capsules are guided serially and/or individually by means of a separating unit (2') through the microwave resonator (3'), which also comprises an adjacent distributor unit (4') by means of which the capsules are arranged parallel for transporting and by means of which the capsules are distributed onto several pathways where the gravimetric weighing cells (5') are located, and which also comprises a computer-aided data collecting unit (7') which is connected to the units (3'), (4') and (5') and ensures that the measurements are correctly assigned to the individual capsules and performs the evaluation and which finally has a reject channel (6') through which capsules of the wrong weight are rejected.

* * * * *